United States Patent [19]

Weeks

[11] Plant 4,282

[45] Jul. 18, 1978

[54] ROSE PLANT

[76] Inventor: O. L. Weeks, 926 W. Philadelphia St., Ontario, Calif. 91761

[21] Appl. No.: 837,747

[22] Filed: Sep. 29, 1977

[51] Int. Cl.[2] ..... A01H 5/00
[52] U.S. Cl. ..... Plt./18
[58] Field of Search ..... Plt./18–19

*Primary Examiner*—Robert E. Bagwill

*Attorney, Agent, or Firm*—Frank B. Robb

[57] ABSTRACT

A new rose variety is disclosed in the hybrid tea class, whose flowers have exceptionally large individual petals and the number of petals on each flower is greater than the usual tea rose, resulting in much more rounded buds, the petals being translucent and creating an almost silken effect, the flowers hold longer than the parents and the canes are less thorny.

1 Drawing Figure

DESCRIPTION OF THE INVENTION

As a result of extensive hybridization, I have created a new and distinct variety of rose plant of the hybrid tea class, identified by me as #76 R 09, which was originated by crossing the seed parent First Prize, U.S. Plant Pat. No. 2,774, and a seedling which is itself the result of much hybridization, the seedling being identified in my records as No. 6742–A-33, this seedling being the pollen parent and in fact being the result of crosses combining Happiness, U.S. Plant Pat. No. 911, Chrysler Imperial, U.S. Plant Pat. No. 1,167, and El Capitan, U.S. Plant Pat. No. 1,796. These three provide coloring which is in turn combined with that of First Prize to produce the coloring hereof as will be apparent from a consideration of the illustration herein.

As a result of this breeding I have produced a new and improved rose variety which is distinguished from its parents as well as from other rose varieties of which I am aware, as evidenced by the following unique combination of principal characteristics which are outstanding in the new variety:

1. A very large, cherry pink to rosey red bloom;
2. The large number of petals as compared with the parents and usual tea rose;
3. The exceptionally large size of individual petals which together with the greater number, produce large round buds;
4. The translucent coloring of the petals;
5. Long lastingness as garden and cut flower;
6. The plant is not leggy and open having relatively few thorns.

A direct comparison with the seed parent, First Prize, indicates that the bloom of my new variety being large and cherry pink to rosey red, is a contrast with the blending of pink shades and reddish overlay of that seed parent First Prize. My new rose has more petals and thus a larger rounder bud compared to the usually long extraordinarily slender bud of the seed parent. The new rose of my creation holds longer as a garden flower and cut rose because of the increased petalage in contrast to its seed parent First Prize. The fact that the seed parent, has less petal substance and is softer than the new rose is a further distinction herein.

In comparison with the pollen parent, it is noted that the instant variety is less leggy and open and has fewer thorns on the canes with foliage leaflets that are waxy as compared with the unpatented parent described.

Asexual reproduction of my new rose variety by budding as performed by me at Chino, Calif., shows that the aforementioned characteristics and distinctions come true to form and are established and transmitted through succeeding propagations.

In the accompanying drawing, there are shown typical specimens of the vegetative growth and flowers of my new variety in different stages of development, depicted in color as nearly true as it is possible reasonably to make the same in a color illustration of this character.

The detailed description which follows and is specifically of my new variety, avails of color terminology in accordance with Munsell's Color Cascade, published by Macbeth Division of Kollmorgen Corp. of Baltimore, Md., except where color terms of ordinary dictionary significance are deemed appropriate:

Type: Hardy; tall; bush; greenhouse and outdoors; seedling; for cut flowers and garden decoration.
Class: Hybrid Tea.
Breeding: Seedling.
*Seed parent.*—First Prize, U.S. Plant Pat. No. 2,774.
*Pollen parent.*—An unamed seedling identified as 6742-A-33.
Propagation: Holds its distinguishing characteristics through successive propagations by budding.

FLOWERS

Locality where grown and observed: Chino, Calif.
Flowers borne: Four to five in regular rounded pyramidal clusters; strong long stems.
Quantity of bloom: Free and abundant both outdoors and in greenhouse.
Continuity: From intermittent to continuous.
Fragrance: Strong.
Bud:
*Peduncle.*—Medium length; heavy caliper; erect; almost smooth; few hairs. Color — Dark green bronze.
*Before calyx breaks.*—Size — From medium to large. Form — Medium length; pointed; with conspicuous neck; with foliaceous appendages on the surface of the bud; slender much cut foliaceous parts extending beyond the tip of the bud equal to ¼ to ½ or more of its length. Color — Light green laced with bronze veins.

*As calyx breaks.*—Color — Light green with bronze veins on outer edge of sepals.

*As petals first open.*—Size — Very large. Form — Long and ovoid. Color — Outside — Bottom segment apple green 21-3 blending into a medium pink red 40-11 with remainder of petal black red 40-15. Inside — Lower segment medium apple green 21-5 blending into a medium pink 39-4, continuing into a candy apple red 40-13 with a medium pink red 40-12, with outer edge of petal a black red 40-15. Opening — Opens up well.

Bloom:

*Size (when fully open).*—Large from 4 to 5 inches in diameter.

*Petalage.*—Double; from 32 to 35 petals arranged regularly.

*Form.*—High centered and ovoid at first, becoming high centered and globular; the petals being at first tightly cupped and rolled outward; becoming later at maturity tightly cupped and rolled outward.

Petals:

*Texture.*—Moderately thick and leathery.

*Appearance.*—Inside velvety; outside satiny.

*Shape.*—Outside — Orbicular; scalloped with flat apex, with 1 to 2 notches. Intermediate — Orbicular; scalloped with apex flat, with 1 to 2 notches. Inside — Obovate; scalloped with apex flat, with 1 notch.

This description of a newly opened flower was made from a rose grown outdoors in the month of September at Ontario, Calif.

*Color.*—Outside petal — Outside surface — Bottom segment a light apple green 23-3 blending to a medium pinkish orange 39-7, continuing into a light pinkish red 40-6. Inside surface — Lower segment is yellow green 23-4, blending into a pinkish orange 37-6, continuing up into a medium pink lavender 41-4. Intermediate petal — Outside surface — Lower segment light yellow green 23-3 blending up into a medium red pink 40-10 with portion of petal having hues of light pinkish lavender 41-4. Inside surface — Bottom segment deep gold 26-6 blending into a deep pinkish red 40-10 with upper part of petal a cotton candy pink 40-9 with light lavender hues 41-4. Inner petal — Outside surface — Lower segment light yellow green 23-3 with a cream streak from bottom to top of petal 23-1, blending up into a medium pink 40-8. Inside surface — Lower segment is dark gold 26-6 blending up into cotton candy pink 39-8.

The following description was made from a rose that was opened for three days outdoors during the month of September at Ontario, Calif.:

*Color.*—Outer petal — Outside surface — Bottom segment light yellow green 23-3 blending into a medium pink 40-7 tinted with orange pink 36-3. Inside surface — Lower segment lemon yellow 25-5 with shadings of light yellow 25-2, with the petal medium pink 40-7 with hues of light pink lavender 41-4. Inner petal — Outside surface — Lower segment medium yellow green 23-4 with a streak of cream 23-1 from the bottom to the tip of petal, with rest of petal a medium pink 40-5. Inside surface — Bottom segment lemon yellow 25-5 blending into a medium pink 40-6 with hues of light pinkish lavender 41-4.

*General color effect.*—Newly opened flower — Overall appearance of cotton candy pink with shades of dark pinkish orange. 3-days open — A medium pinkish orange to a light pink with middle petals a pink peach.

*Behavior.*—Drop off cleanly.

*Flower longevity.*—On bush in garden — 3 to 4 days in October. Cut flowers grown outdoors kept at living room temperatures 3 to 4 days in October.

REPRODUCTIVE ORGANS

Stamens: Arranged regularly about pistils, mixed with petaloids and tucked in calyx.

Filaments: Short to medium length, most with anthers. Color — Yellow.

Anthers: Small to medium, all open at once. Color — Yellow.

Pollen: Abundant. Color — Gold yellow.

Pistils: Many.

Styles: Uneven; medium to long length; medium caliper and bunched.

Stigma: Color — White.

Ovaries: All enclosed in calyx.

Hips: None observed.

Sepals: Permanent; long; spear-shaped and recurved.

Seeds: None observed.

PLANT

Foliage:

*Leaves.*—Compound of 5 leaflets; moderately abundant; medium to large size; moderately heavy and leathery; wrinkled.

*Leaflets.*—Shape — Ovate with apex obtuse; margin irregularly serrate.

*Color.*—Mature — Upper surface — Light to dark green 20-14. Under surface — Light grey green 21-9. Young — Upper surface — Very bright bronze 40-15. Under surface — Light satin bronze 40-15.

Foliage:

*Rachis (the supporting stem of the compound leaf).*—Light to medium weight. Upper side — Grooved with few hairs. Under side — Sparsely thorny.

*Stipules.*—Moderately long; moderately narrow with short points turning out at an angle of less than 45°.

*Disease and insect resistance.*—Average resistance to powdery mildew.

Growth:

*Habit.*—Upright; much branched.

*Growth.*—Moderately to very vigorous.

*Canes.*—Medium caliper.

*Main stems.*—Color — Dull grey green. Large prickles — Many; long straight with short base. Color — Brown. Small prickles — Color — Brown. Hairs — None.

*Branches.*—Color — Yellowish green. Large prickles — Many; long; hooked downward; long narrow base. Color — Yellowish brown. Small prickles — None. Hairs — None.

*New shoots.*—Color — Bronze. Large prickles — Very few; short hooked downward; long narrow base. Color — Bronze. Small prickles — None. Hairs — None.

I claim:

1. A new and distinct variety of Rose plant of the hybrid tea class, substantially as herein shown and described, characterized particularly as to novelty by the unique combination of a very large cherry pink to a rosey red bloom, the bloom comprising exceptionally large individual petals, with a large quantity of petals, the large quantity and size of petals providing a much more rounded large bud, the petals being translucent and appearing to be almost silken and of great substance, the ability to hold longer as a garden flower and cut rose, and the plant being less leggy and open with fewer thorns and more waxy foliage leaflets.

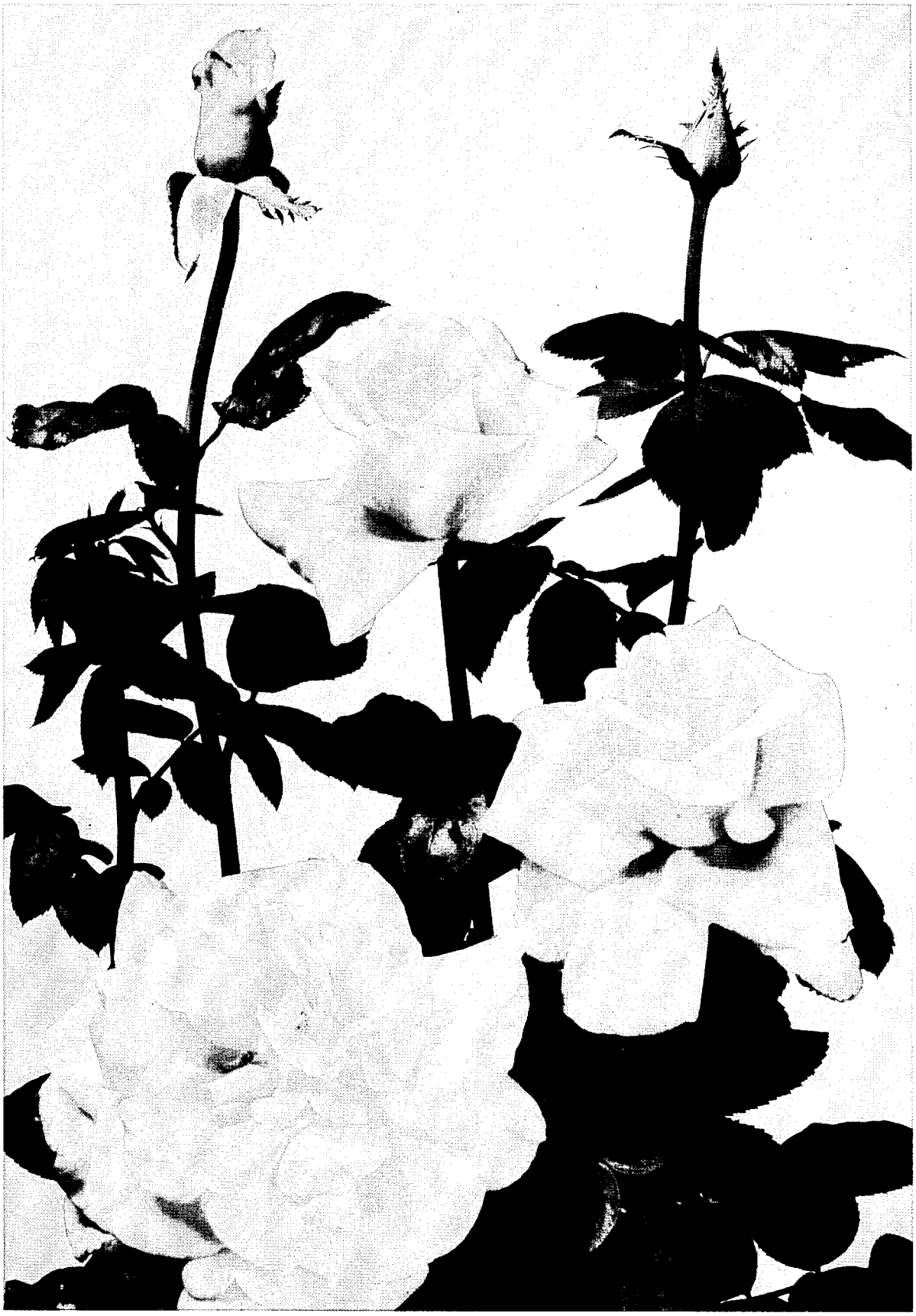

* * * * *